United States Patent [19]
Schwartz et al.

[11] Patent Number: 6,015,405
[45] Date of Patent: Jan. 18, 2000

[54] DEVICE FOR FORMING HOLES IN TISSUE

[75] Inventors: Robert S. Schwartz; David R. Holmes, both of Rochester; Robert A. VanTassel, Excelsior, all of Minn.

[73] Assignee: Tricardia, L.L.C., Excelsior, Minn.

[21] Appl. No.: 09/009,135

[22] Filed: Jan. 20, 1998

[51] Int. Cl.$^7$ .............................. A61B 17/00; A61B 8/00
[52] U.S. Cl. .............................. 606/16; 606/41
[58] Field of Search .............................. 606/1, 7, 15, 16, 606/17, 108, 28, 32, 41, 47, 50, 51, 39, 40; 604/22

[56] References Cited

U.S. PATENT DOCUMENTS

| | | |
|---|---|---|
| 3,659,610 | 5/1972 | Cimber . |
| 4,411,653 | 10/1983 | Razi . |
| 5,042,461 | 8/1991 | Inoue et al. . |
| 5,061,255 | 10/1991 | Greenfeld et al. . |
| 5,186,712 | 2/1993 | Kelso et al. . |
| 5,190,552 | 3/1993 | Kelman .................................. 606/108 |
| 5,260,020 | 11/1993 | Wilk et al. . |
| 5,336,252 | 8/1994 | Cohen .................................. 607/119 |
| 5,411,509 | 5/1995 | Hilal . |
| 5,423,829 | 6/1995 | Pham et al. .................................. 606/1 |
| 5,514,128 | 5/1996 | Hillsman et al. .......................... 606/7 |
| 5,527,290 | 6/1996 | Zadini et al. . |
| 5,549,644 | 8/1996 | Lundquist et al. ........................ 604/22 |
| 5,685,322 | 11/1997 | Sung et al. .............................. 606/108 |
| 5,814,062 | 9/1998 | Sepetka et al. .......................... 606/198 |
| 5,876,340 | 3/1999 | Tu et al. .................................. 606/41 |

*Primary Examiner*—John P. Leubecker
*Assistant Examiner*—Sonya Harris Ogugua
*Attorney, Agent, or Firm*—Nikolai, Mersereau & Dietz, P.A.

[57] ABSTRACT

A surgical instrument for creating holes of a predetermined diameter and depth in body tissue comprises a tubular catheter having a compression spring affixed at its distal end and attached to the distal end of that spring is a tissue ablating device which may, for example, comprise an electrosurgical monopolar or bipolar electrode that is connected by conductors extending through the lumen of the catheter to an electrosurgical generator at its proximal end. When the instrument is brought in contact with target tissue with a force sufficient to compress the coils of the spring against one another and then ablating energy applied, tissue will be removed as the spring is allowed to expand out to its uncompressed length. The depth of the hole thus created is equal to the difference between the lengths of the spring when compressed and uncompressed. If desired, a suitable drug can be delivered into the thus created hole via a lumen in the catheter.

11 Claims, 2 Drawing Sheets

DEVICE FOR FORMING HOLES IN TISSUE

BACKGROUND OF THE INVENTION

I. Field of the Invention

This invention relates generally to surgical instruments, and more particularly to a device for creating holes of a predetermined depth into body tissue.

II. Discussion of the Prior Art

In conducting various surgical procedures, it often becomes desirable to form a hole of a given diameter through tissue in such a way that the depth of penetration can also be accurately controlled. A procedure referred to as transmyocardial revascularization (TMR) may be applied endocardially or epicardially in revascularizing ischemic tissue. Here, small holes are drilled in the myocardium to allow blood to reach areas of the heart normally served by arteries or arterioles but which may have become occluded due to coronary artery disease. Also, where an artery has become so obstructed that a guide wire commonly used in percutaneous transluminal coronary angioplasty procedures cannot be passed, a need exists for an instrument to bore through the stenotic lesion in a controlled fashion so that the affected artery is not perforated.

Instruments especially designed for carrying out atherectomy procedures in larger arteries generally involve a catheter supporting a rotatable cutting blade on a distal end thereof for cutting through stenotic lesions and with suction being applied to remove the debris created during the cutting procedure. Generally speaking, the depth of penetration is controlled strictly by the operator in advancing the catheter. The instrument itself has no built-in structure for controlling the depth of penetration.

A need therefore exists for a surgical instrument that can safely be used in either open surgical procedures or in laparoscopic or intravascular procedures to create a hole of a predetermined diameter and desired depth dimension in multiple incremental uniform steps in target tissue structures.

SUMMARY OF THE INVENTION

The present invention provides a surgical instrument for forming holes of a predetermined diameter and depth dimension in selected tissue. In accordance with a preferred embodiment, it comprises an elongated catheter or tubular sheath having a proximal end, a distal end and a lumen extending between these two ends. A compression spring or spring-loaded cutting tip of a predetermined length dimension, when uncompressed is affixed to and extends from the distal end of the catheter. A tissue ablating device is carried by the compression spring and is adapted to be pressed against the selected tissue in which a hole is to be bored with sufficient force to compress the spring. When the tissue ablating device is energized, a portion of the selected tissue abutting the ablating device is removed, allowing the spring to expand to its uncompressed length dimension. Thus, the depth of penetration is equal to the difference between the compressed and uncompressed length of the coil spring.

The tissue ablating device may comprise an electrode on the spring tip adapted to be energized by RF energy or, alternatively, an optical fiber adapted to be energized by a source of laser energy. A third alternative would be to use an ultrasonic transducer on the spring tip capable of crushing and emulsifying animal tissue which then can be aspirated through the lumen of the catheter.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
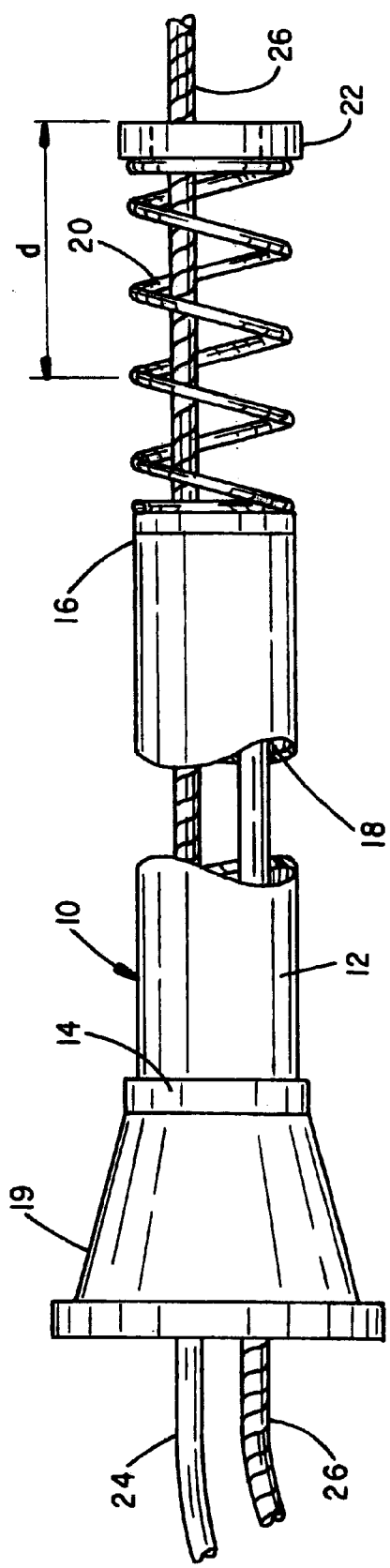
FIG. 1 is a side elevational view of the tissue drilling instrument of the present invention.

Referring to FIG. 1, there is indicated generally by numeral 10 a surgical instrument for forming holes in tissue structures where the holes are of a predetermined diameter and depth dimension. It comprises an elongated tubular member 12 having a proximal end 14 and a distal end 16 and with a lumen 18 extending therebetween. Affixed to the proximal end of the tubular body member 12 is a molded plastic hub 19 which may take on a variety of configurations but in FIG. 1 is shown as a simple female Luer connector.

Affixed to the distal end of the tubular body member 12 is a compression spring 20 of a predetermined length dimension such that the difference, d, between its fully compressed condition and its uncompressed condition will control the depth of the hole to be formed in the tissue, all as will be described in greater detail below.

Affixed to the distal end of the compression spring 20 is a tissue ablating device 22. The tissue ablating device 22 may comprise an electrosurgical electrode (monopolar or bipolar) that is adapted to be coupled, via an insulated conductor, passing through the lumen 18 to a radio frequency electrosurgical generator of conventional design (not shown).

The tissue ablating device 22 may alternatively comprise a lens for focusing laser energy delivered through the tubular catheter body 12 by an optical fiber whose proximal end is coupled to a source of laser light.

The tissue ablating device 22 may also be an ultrasonic transducer that is connected by electrical conductors passing through the lumen 18 of the catheter for connection to a ultrasound power supply (not shown) coupled to the proximal end of the instrument 10.

Figure 2:
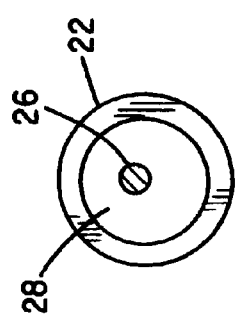
FIG. 2 is a right end view of the instrument of FIG. 1.

The catheter 12 may be rigid when intended for use in an open surgical procedure or a laparoscopic procedure, but for intravascular applications, the catheter body 12 is preferably formed from a flexible plastic material, such as are commonly used in the manufacture of diagnostic coronary catheters that may be introduced, for example, into the femoral artery and advanced over a guide wire until the tissue ablating device is disposed adjacent target tissue to be penetrated. To accommodate passage over a guide wire, such as guide wire 26 in FIG. 1, it is preferable that the tissue ablating device 22 be provided with an opening 28 therethrough, as shown in the distal end view of FIG. 2. Also, the opening may permit drug delivery to the target site via the guidewire lumen.

Figure 3:
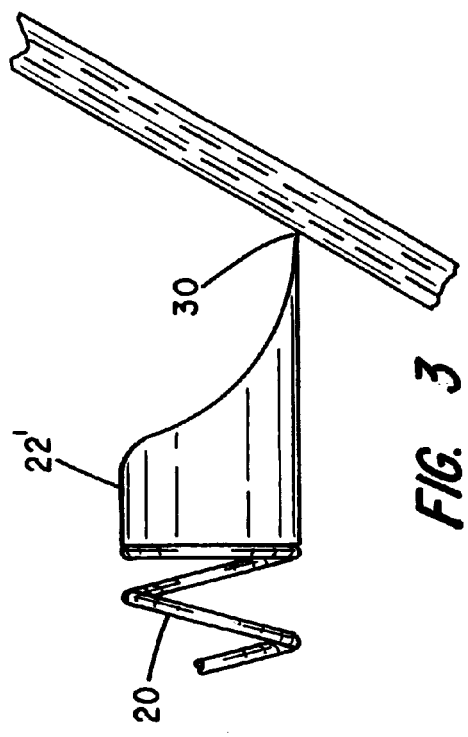
FIG. 3 is a partial side view of an alternatively shaped electrode for use with the instrument of FIG. 1.

FIG. 3 illustrates an alternative shape configuration which may be advantageously used when being advanced against tissue that is at an angle to the longitudinal axis of the catheter. By providing a sharpened tip 30 on the tissue ablating device 22', any tendency for the tissue ablating device to slide along the tissue structure will be inhibited.

In using the hole forming instrument 10 of FIG. 1, the operator will advance the catheter 12 until the tissue ablating device 22 on the distal end thereof is brought into engagement with the target tissue. The catheter will then continue to be advanced with sufficient force to compress the spring 20 so that its coils abut one another. Now, by energizing the tissue ablating device 22 while holding the catheter stationary, the tissue structure in which it is in contact will be ablated allowing the spring 20 to extend its full length, creating a hole in the tissue whose depth is the difference between the compressed length and uncompressed length of the spring 20. If it is desired to increase the depth of penetration into the tissue, after de-energizing the tissue ablating device 22, the catheter 12 can again be advanced in the distal direction to the point where the spring 20 is again fully compressed. At this point, a second energization of the tissue ablating device 22 will again result in the expansion of the spring 20 to its full length thereby effectively doubling the hole depth. Because each step is of a precise, known length, the composite hole depth can be accurately determined.

Figure 4:
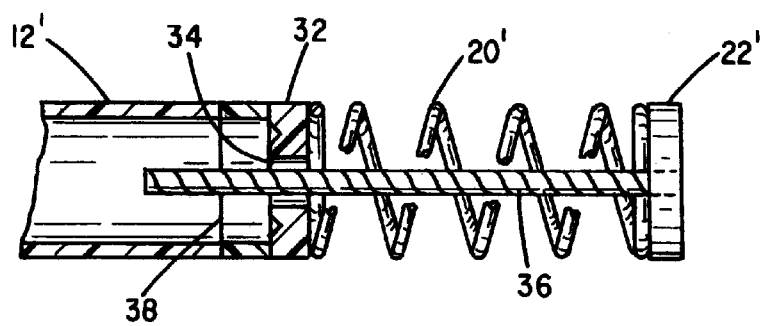
FIG. 4 is a partial side view of the distal end portion of an alternative embodiment in which the penetration depth of the instrument can be varied.

In the embodiment of FIG. 1, the extent of advancement of the tissue ablating device into the target tissue upon energization is determined by the particular spring 20 employed on the catheter. FIG. 4, which shows only the distal end portion of the instrument of FIG. 1, is designed to allow the surgeon to set the distance that the spring is allowed to expand. Here, the catheter body 12 has an end cap 32 having a clearance bore 34 formed through it and an annular pattern of ratchet teeth formed on its proximal facing side. A spring 20' is affixed to the end cap 32 and attached to the opposite end thereof is a tissue ablating device 22'. Completing the assembly is a threaded screw 36 that is affixed to the device 22' and that passes through the center of the helix comprising compression spring 20' and through the clearance bore 34 of the end cap 32 into a nut 38 having matching ratchet teeth on its distal facing surface. By rotating the device 22', the degree of extension of the spring and its attached tissue ablating device becomes adjustable. More particularly, with the teeth on the nut 38 mating with those on the end cap 32, rotation of screw 36 adjusts the span between the end cap and the ablating device 22'. With the device abutting the target tissue, a pushing force applied to the catheter 12' will disengage the ratchet teeth on the nut from those on the end cap and will compress the spring to the point where its coils abut one another. Now, when the energy is applied to the ablating device 22' and tissue is removed, the spring can only expand to the extent permitted by the screw 36.

Figure 5:
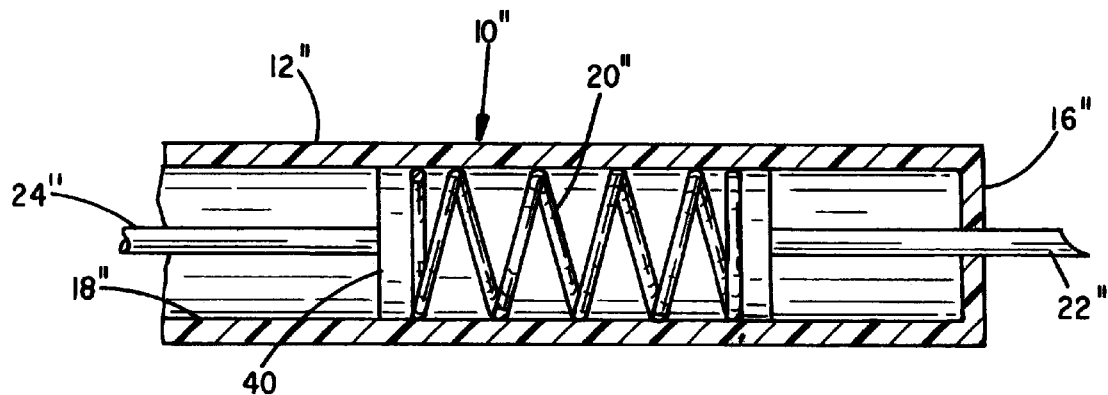
FIG. 5 is a partial side view of the distal end portion of a further alternative embodiment having a telescoping ablation member.

FIG. 5 is a cross-sectional and partial view of the distal end portion of the hole forming catheter comprising a further preferred embodiment. In this arrangement, the tissue ablating device 22' is slidingly received within the lumen 18" of the catheter body 12" and a portion thereof projects beyond the distal end 16" of the catheter body. Formed internally of the lumen 18" is an annular stop 40 against which the proximal end of the spring member 20" abuts. The distal end of the spring 20' cooperates with the tissue ablating device 22', normally urging it in the distal direction. Depending on the nature of the tissue ablating device, energization therefore may be conveyed either over electrical conductors 24" that extend through the lumen 18" or via an optical fiber where laser energy is employed.

As with the above-described embodiments, when used, the catheter 10" is percutaneously inserted into the body and routed therethrough until the tissue ablating device 22" abuts the target tissue where a hole is to be created. The catheter is continued to be advanced until the spring 20" is fully compressed such that its coils abut one another. While holding the catheter stationary, the tissue ablating device 22" is appropriately energized with electrical or light energy to thereby ablate tissue against which it is placed. As the tissue disintegrates, the spring 20" is allowed to expand and advance the tissue ablating device 22" until the spring is fully extended. If a hole of an increased depth is desired, the foregoing step may be repeated a number of times with each iteration resulting in a penetration distance equal to the difference between the compressed length and uncompressed length of the spring 20".

With either embodiment, it is possible to inject a drug into the newly created tissue perforation by coupling a syringe to the Luer fitting 19 and injecting the drug through the lumen 18 and out the central opening of the annular tissue ablating device 22.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. Apparatus for forming holes of a predetermined depth and diameter dimension in selected tissue comprising:
   (a) an elongated catheter having a proximal end a distal end and a lumen extending therebetween;
   (b) a compression spring having first and second ends, the spring being of a predetermined length dimension when uncompressed with the first end being affixed proximate the distal end of the catheter and with the spring extending longitudinally therefrom; and
   (c) a tissue ablating device operatively coupled to the second end of said compression spring such that upon actuation, said spring expands linearly to provide longitudal displacement of said tissue ablating device, and adapted to be pressed against said selected tissue with sufficient force to compress said spring with subsequent energization of the tissue ablating device ablating tissue distal to the tissue ablating device and allowing the spring to expand to its uncompressed length dimension.

2. The apparatus as in claim 1 wherein the tissue ablating device comprises an electrosurgical electrode.

3. The apparatus as in claim 2 and further including at least one electrical conductor passing through said lumen and conductively connected to the electrosurgical electrode.

4. The apparatus as in claim 2 wherein the electrosurgical electrode is an annulus.

5. The apparatus as in claim 2 wherein the electrosurgical electrode includes a sharp point.

6. The apparatus as in claim 1 wherein the tissue ablating device comprises an optical fiber and a source of laser energy coupled to said optical fiber.

7. The apparatus as in claim 6 wherein the optical fiber extends through said lumen.

8. The apparatus as in any one of claims 2 and 6 wherein the compression spring and at least a portion of said tissue ablating device is contained within said lumen.

9. A method for forming holes of a predetermined length in selected tissue in a patient comprising the steps of:
(a) providing a catheter having a proximal end, a distal end and a lumen extending therebetween, said catheter having a compression spring of said predetermined incremental length when uncompressed disposed on said distal end of the catheter with the spring supporting a tissue ablating device thereon;
(b) routing said catheter percutaneously to reach said selected tissue;
(c) pressing the tissue ablating device against the selected tissue with a force sufficient to fully compress the spring;
(d) energizing the tissue ablating device to ablate the selected tissue sufficient to allow the spring to expand to its predetermined incremental length; and
(e) repeating steps (c) and (d) until a hole of a desired length in the tissue has resulted.

10. The method of claim 9 and further including the step of injecting a drug through the lumen and into the hole following step (e).

11. Apparatus for forming holes of a predetermined depth and diameter dimension in a selected tissue comprising:
(a) an elongated catheter having a proximal end, a distal end and a lumen extending therebetween;
(b) a compression spring of a predetermined length dimension when uncompressed affixed proximate the distal end of the catheter; and
(c) a tissue ablating device operatively coupled to said compression spring, the tissue ablating device including an optical fiber extending through said lumen and a source of laser energy coupled to the optical fiber, the tissue ablating device adapted to be pressed against said selected tissue with sufficient force to compress said spring and with subsequent energization of the source of laser energy, ablating tissue distal to the compression spring and allowing the spring to extend to its uncompressed length dimension.

\* \* \* \* \*